United States Patent [19]

Ushio et al.

[11] Patent Number: 5,728,589
[45] Date of Patent: Mar. 17, 1998

[54] IMMUNOASSAY METHOD

[75] Inventors: Yoshihiro Ushio; Katsuji Aoki, both of Amagasaki, Japan

[73] Assignee: Wako Pure Chemical Industries, Ltd., Osaka, Japan

[21] Appl. No.: 291,895

[22] Filed: Aug. 17, 1994

[30] Foreign Application Priority Data

Aug. 24, 1993 [JP] Japan .................................. 5-230866
Aug. 24, 1993 [JP] Japan .................................. 5-230867

[51] Int. Cl.$^6$ .................................................. G01N 33/542
[52] U.S. Cl. ........................... 436/543; 436/537; 436/547; 436/815; 436/817; 436/820
[58] Field of Search ............................... 436/537, 543, 436/547, 815, 817, 820

[56] References Cited

U.S. PATENT DOCUMENTS

| | | | |
|---|---|---|---|
| 5,168,057 | 12/1992 | Oh et al. | 435/174 |
| 5,196,351 | 3/1993 | Harris et al. | 436/501 |
| 5,219,764 | 6/1993 | Huber et al. | 436/536 |

FOREIGN PATENT DOCUMENTS

| | | |
|---|---|---|
| 0 315 317 | 5/1989 | European Pat. Off. . |
| 0 451 810 | 10/1991 | European Pat. Off. . |
| 0 524 583 | 1/1993 | European Pat. Off. . |
| 2 098 730 | 11/1982 | United Kingdom . |
| 2 261 948 | 6/1993 | United Kingdom . |

OTHER PUBLICATIONS

Derwent Publications, Ltd., Database WPI, Section ch, Week 9416; JP A-06 082 449; 22 Mar. 1994, Abstract.

C. Oh et al., Clin. Chim. Acta, vol. 218, No. 1, pp. 59–71 (1993).

*Primary Examiner*—Mary E. Ceperley
*Attorney, Agent, or Firm*—Armstrong, Westerman, Hattori, McLeland & Naughton

[57] ABSTRACT

The use of an antigen (or antibody) previously modified with a hapten makes the immunoassay of a trace component (analyte) on the basis of a change of turbidity or scattered light intensity caused by antigen-antibody reaction rapid and easy with high accuracy and high reproduction.

10 Claims, 6 Drawing Sheets

IMMUNOASSAY METHOD

BACKGROUND OF THE INVENTION

This invention relates to an immunoassay method which permits specific, rapid and accurate quantitation of trace components in body fluids such as serum, plasma and urine.

In recent years, autoanalyzers capable of analyzing many samples for many items at the same time have spread, and attempts have been made to apply a method for immunoassay of a trace component utilizing antigen-antibody reaction to the autoanalyzers.

Typical examples of method applicable to the autoanalyzers are so-called immunoturbidimetry in which an objective component is measured by measuring a turbidity change caused by antigen-antibody reaction, and so-called immunonephelometry in which an objective component is measured by measuring a scattered light intensity change caused by antigen-antibody reaction.

These methods, however, are disadvantageous in that when the amount of an analyte to be measured in a sample is small (namely, when the concentration of the analyte is low), the measured value of the analyte is lower than its theoretical value, so that the analyte cannot be accurately measured.

In the above methods, for removing such a defect, there are investigated, for example, a method of adding a large amount of an antigen-antibody reaction accelerator such as polyethylene glycol (PEG) or chondroitin sulfate to a measuring system, and a method of increasing the absolute amount of a sample. Both of these methods, however, are disadvantageous in that measurement errors are caused by substances present in a sample together with an analyte to be measured or by an insoluble material produced by a non-specific reaction. Therefore, there is a desire to seek further improvement in the methods.

SUMMARY OF THE INVENTION

This invention was made in view of such conditions and is intended to provide an immunoassay method which permits accurate, highly-reproducible, rapid and easy measurement of an analyte to be measured, even in a low concentration range and is applicable to autoanalyzers.

This invention provides a method for immunoassay of a trace component (analyte) on the basis of a change of turbidity or scattered light intensity caused by antigen-antibody reaction, which uses an antigen previously modified with a hapten, as antigen against an antibody to be measured.

This invention also provides a method for immunoassay of a trace component (analyte) on the basis of a change of turbidity or scattered light intensity caused by antigen-antibody reaction, which uses an antibody previously modified with a hapten, as antibody against an antigen to be measured.

This invention also provides a reagent composition for immunoassay comprising an antigen against an antibody to be measured, said antigen being previously modified with a hapten.

This invention also provides a reagent composition for immunoassay comprising an antibody against an antigen to be measured, said antibody being previously modified with a hapten.

This invention also provides a reagent composition for immunoassay comprising a combination of a reagent comprising an antigen against an antibody to be measured, said antigen being previously modified with biotin; and a reagent comprising avidin or streptoavidin.

In addition, this invention provides a reagent composition for immunoassay comprising a combination of a reagent comprising an antibody against an antigen to be measured, said antibody being previously modified with biotin; and a reagent comprising avidin or streptoavidin.

DESCRIPTION OF THE PREFERRED EMBODIMENTS

Figure 1:
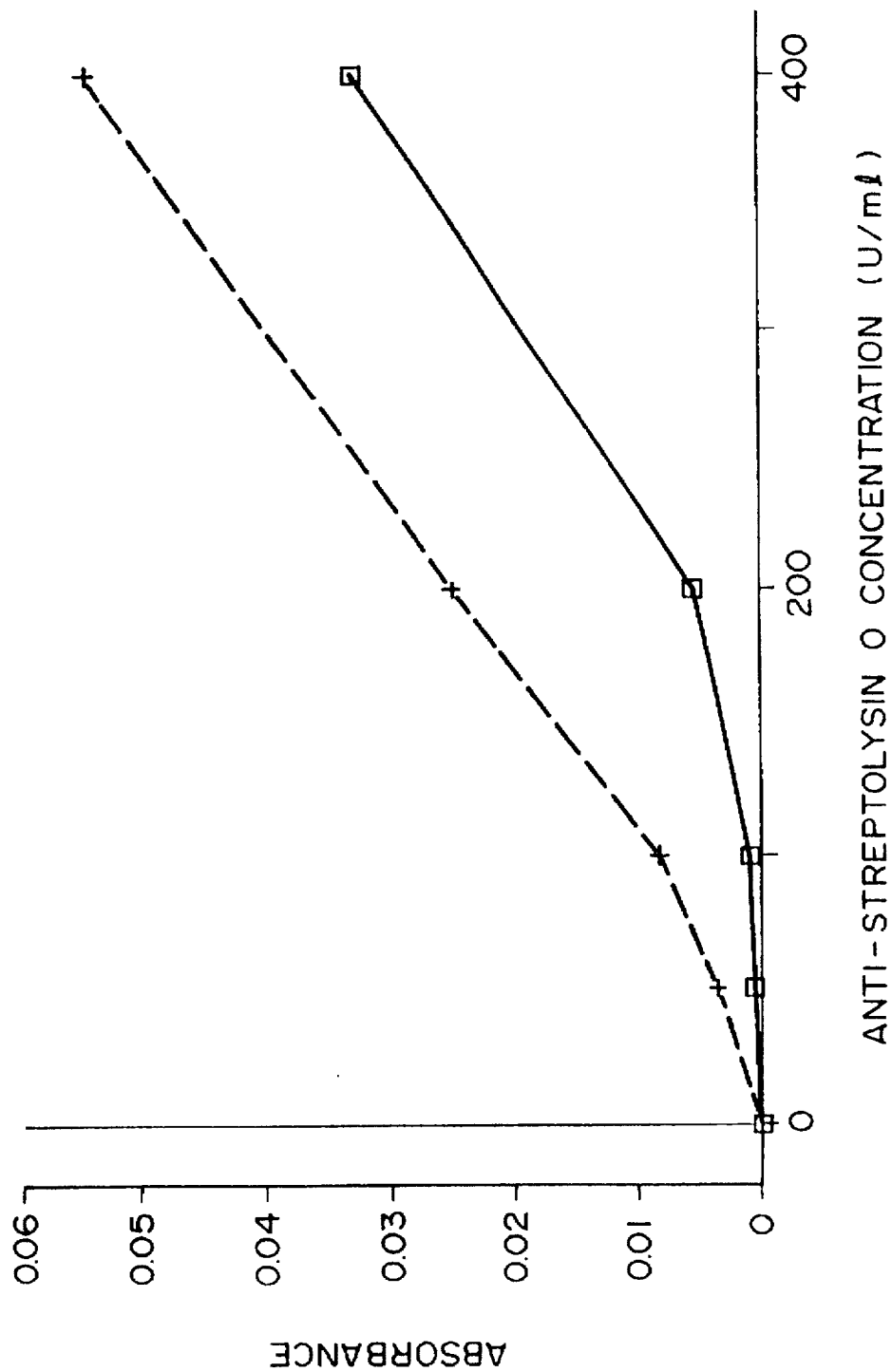
FIG. 1 shows a calibration curve obtained in Example 1.

In order to find a method for enhancing measuring sensitivity for an analyte to be measured, in a low concentration range without any influence of substances present together with the analyte and measurement error caused by a non-specific reaction, the present inventors earnestly investigated and consequently found that a high reaction sensitivity and a calibration curve showing good linearity can be obtained even in a low concentration range by modifying an antigen against an antibody to be measured (or an antibody against an antigen to be measured), which is added to a reagent, with a hapten such as a compound having a benzene ring or a compound having a heterocyclic ring. Thus, the present invention has been accomplished.

As the hapten used in this invention for modifying an antigen (or antibody), any material may be used without particular limitation so long as it is generally known as hapten. Particularly preferable examples of the hapten are compounds having a benzene ring and compounds having a heterocyclic ring.

As the compounds having a benzene ring which can be used as hapten in this invention, there can be exemplified compounds having, for example, a substituted or unsubstituted phenyl, tolyl, xylyl or naphthyl group. The substituent includes, for example, unsubstituted alkyl groups such as methyl group, ethyl group, propyl group and butyl group (which may be either linear or branched), substituted alkyl groups (having as the substituent a hydroxyl group, alkoxy group such as methoxy group, ethoxy group, propoxy group and butoxy group (which may be either linear or branched), carboxyl group, sulfo group, halogen atom such as chlorine, bromine and iodine, or the like), alkoxy groups such as methoxy group, ethoxy group, propoxy group and butoxy group (which may be either linear or branched), nitro group, acetyl group, carboxyl group, sulfo group, and halogen atoms such as chlorine, bromine and iodine.

Preferable specific examples of the compounds having a benzene ring which can be used in this invention are p-nitrophenylacetic acid, 4-methylbenzoic acid and 3-(1-naphthyl)propionic acid.

Preferable examples of the compounds having a heterocyclic ring which can be used as hapten in this invention are compounds having a heterocyclic group such as thiazolyl, thienyl, furanyl, pyranyl, pyrrolyl, imidazolyl, pyrazolyl, isothiazolyl, isoxazolyl, pyrimidinyl, pyridazinyl, indolyl, purinyl, quinolyl, isoquinolyl, pyrazolinyl, indolinyl, morpholino, biotinyl or the like (all of these groups may have a substituent). As the substituent on the heterocyclic group, there can be exemplified unsubstituted alkyl groups such as methyl group, ethyl group, propyl group and butyl group (which may be either linear or branched), substituted alkyl groups (having as the substituent a hydroxyl group, alkoxy group such as methoxy group, ethoxy group, propoxy group and butoxy group (which may be either linear or branched), carboxyl group, sulfo group, halogen atom such as chlorine, bormine and iodine; or the like), alkoxy groups such as methoxy group, ethoxy group, propoxy group and butoxy group (which may be either linear or branched), nitro group, acetyl group, carboxyl group, sulfo group, and halogen atoms such as chlorine, bromine and iodine.

Preferable specific examples of the compounds having a heterocyclic ring which can be used in this invention are biotin, 2-thienylacetic acid, indole-butyric acid and pyrrole-2-carboxylic acid.

In the present invention, as a method for modifying an antigen or antibody with the compound having a benzene ring, the following methods, for example, can be exemplified.

For example, modification of an antigen or antibody with p-nitrophenylacetic acid can easily be carried out by introducing a succinimide group into p-nitrophenylacetic acid by a conventional method [for instance, J. Amer. Chem. Soc., vol. 85, 3039(1963) and J. Amer. Chem. Soc., vol. 86, 1839(1964)], and reacting the resulting compound with the antigen or antibody by a conventional method [for instance, Z. Anal. Chem., vol. 279,143(1976); J. Clin. Endocrinol. Metab., vol. 44, 91(1977); and Biochem. Biophys. Acta., vol. 403, 131(1975)]. When a commercially available SNPA (N-succinimidyl-p-nitrophenylacetate) reagent manufactured by DOJINDO LABORATORIES by introducing a succinimide group into p-nitrophenylacetic acid is used, the succinimide group introduction step can be omitted, so that the modification procedure can be simplified.

Examples of other methods are a method of introducing a maleimide group into the compound having a benzene ring by a conventional method [for example, J. Pharm. Dyn., vol. 4, 812–819(1981)] and reacting the resulting compound with the thiol group of an antigen or antibody [for example, Annals of the New York Academy of Science, vol. 254, 203(1975)]; and a method of introducing a hydrazino group into the compound having a benzene ring by a conventional method [for example, J. Biol. Chem., vol. 172, 71(1948)], and reacting the resulting compound with an aldehyde-modified antigen or antibody [for example, Biotech. Appln. Biochem., vol. 9, 488–496(1987)].

As to the degree of the modification of an antigen or antibody with the compound having a benzene ring, the amount of the compound is usually about 0.2 to about 10 moles, preferably about 1 to about 5 moles, per mole of the antigen or antibody. When the degree of the modification with the compound having a benzene ring is too high, there is a problem, for example, in that the insolubility of the antigen or antibody is increased or that the antigen-antibody reaction is inhibited. When the degree of the modification is too low, there is a problem, for example, in that the sensitivity does not reach a desired value. Therefore, care should be taken in the modification.

Preferable examples of method for attaching the compound having a heterocyclic ring, such as biotin to an antigen or antibody are a method of reacting a commercially available biotinylation reagent [for example, biotin having a succinimide group introduced thereinto (e.g. N-hydroxysuccunimidobiotin) or a product obtained by combining N-hydroxysuccinimide (NHS) and biotin through a spacer] with the amino group of an antibody or antigen protein; a method of reacting, for example, a commercially available N-[6-(biotinamide)hexyl]-3'-(2'-pyridyldithio)propionamide (biotin-HPDP) or N-iodoacetyl-N-biotinylhexylenediamine with the thiol group of an antigen or antibody [for instance, Annals of the New York Academy of Science, vol. 254, 203(1975)]; and a method of reacting biotin (or other compound having a heterocyclic ring) having a hydrazino group introduced thereinto with the aldehyde group of an aldehyde-modified antigen or antibody [for instance, J. Biol. Chem., vol. 172, 71(1948) and Biotech. Appl. Biochem., vol. 9, 488–496(1987)].

As to the degree of the modification of an antigen or antibody with the compound having a heterocyclic ring, the amount of the compound is usually about 0.2 to about 10 moles, preferably about 1 to about 5 moles, per mole of the antigen or antibody. When the degree of the modification with the compound having a heterocyclic ring is too high, there is a problem, for example, in that the insolubility of the antigen or antibody is increased or that the antigen-antibody reaction is inhibited. When the degree of the modification is too low, there is a problem, for example, in that the sensitivity does not reach a desired value. Therefore, care should be taken in the modification.

In the method of this invention, preferable examples of the antigen used after being modified with a hapten are streptolysin O (SLO), rheumatoid factor (RF) and hepatitis B type virus surface antigen (HBs).

The antibody used after being modified with a hapten is not critical and may be either a monoclonal antibody or a polyclonal antibody. Preferable specific examples of the antibody are anti-C-reactive protein (anti-CRP) antibody, anti-immunoglobulin G (anti-IgG) antibody, anti-immunoglobulin A (anti-IgA) antibody, anti-immunoglobulin M (anti-IgM) antibody, anti-albumin antibody, anti-C3 antibody, anti-C4 antibody and anti-α-fetoprotein (anti-AFP) antibody.

It is sufficient that all of other reagents, measuring conditions (reaction temperature, reaction time, measuring wavelength, measuring apparatus, etc.) and the like which are employed for practicing the measuring method of this invention are selected from those employed in a conventional immunoturbidimetry or immunonephelometry method. That is, it is sufficient that the measuring method of this invention is practiced according to a measuring procedure used in a conventional immunoturbidimetry or immunonephelometry method, except for using an antigen or antibody modified with a hapten in the manner described above. In the measuring method of this invention, there can be used without exception all of autoanalyzers, spectrophotometers and the like which are usually used in the art.

Specific examples of buffer solution used in the measuring method of this invention are all of those usually used in measuring methods using antigen-antibody reaction, such as Tris buffers, phosphate buffers, veronal buffers, borate buffers, Good's buffers, etc. The pH of the buffer solution is not critical so long as it does not inhibit the antigen-antibody reaction. Usually, the pH is preferably in the range of 5 to 9.

According to the method of this invention, a calibration curve showing good linearity even in a low concentration range can be obtained because the reaction sensitivity is high even when the concentration of an analyte to be measured is low. Although the reason is unexplained, the following, for example, is conjectured. By the modification of an antigen or antibody, which participates the reaction, with a hapten such as a compound having a benzene ring or a compound having a heterocyclic ring, the hydrophobicity of the antigen or antibody is increased and the hydrophobicity of the antigen-antibody complex produced by the reaction is also inevitably increased. Therefore, the precipitation of the desired antigen-antibody complex as insoluble material from the reaction solution is facilitated even at a low concentration.

In this invention, when an amount of an analyte to be measured is small (such as rheumatoid factor, C-reactive protein, etc), it is possible to enhance the reaction sensitivity in a low concentration range and obtain a calibration curve showing good linearity by carrying out an objective measurement using an antigen against an antibody to be measured (or an antibody against an antigen to be measured) which is modified using biotin as hapten in the presence of avidin or streptoavidin.

Avidin-biotin reaction is highly specific and the bonding strength between avidin and biotin is strong. Therefore, in enzyme immunoassay and radio-immunoassay, avidin-biotin reaction is used for combining a solid phase with an antigen-antibody reaction product or combining an antibody or the like with a labeling substance. In latex photometric immunoassay and carrier agglutination method, avidin-biotin reaction is used for combining a carrier with an antigen (or antibody). However, few cases are known where avidin-biotin reaction is used together with antigen-antibody reaction in carrying out immuno-turbidimetry or immunonephelometry, which utilizes the antigen-antibody reaction. It is really surprising that the co-use of avidin-biotin reaction markedly enhances the measuring sensitivity attained when the amount of an analyte to be measured in a sample is small (namely, the measuring sensitivity in a low concentration range).

As the avidin or streptoavidin used in this invention, a commercially available one may be used as it is. The quality and purity of the avidin or streptoavidin are not particularly limited. The amount of the avidin or streptoavidin used is not critical and is varied depending on the amount of biotin used for modifying an antigen (or antibody) against an analyte to be measured, and measurement items. Usually, the concentration of the avidin or streptoavidin in the reaction solution is properly chosen in the range of 0.01 to 1,000 µg/ml, preferably 0.1 to 100 µg/ml, more preferably 5 to 100 µg/ml.

When an objective measurement is carried out in the presence of avidin or streptoavidin, the present invention's reagent composition for immunoassay in which the reaction of avidin (or streptoavidin) with biotin is utilized can be used in the form of a single reagent. But since turbidity on the basis of the reaction of avidin (or streptoavidin) with biotin is produced slowly, it is preferable for reagent stability to prepare the composition as a reagent form composed of two separate groups, i.e., a reagent group containing avidin or streptoavidin and a reagent group containing a biotin-modified antigen or a biotin-modified antibody.

In the present inventions, a method without using an avidin (or streptavidin) is preferable comparing with a method of using an avidin (or streptavidin). That is, since turbidity on the basis of the reaction of avidin (or streptavidin) with biotin is produced slowly, the method of using an avidin (or streptavidin) is disadvantageous in that the reagent for the method is low in stability, a blank value of the reagent increases slowly, etc.

This invention is more concretely explained below with reference to Examples, which are not by way of limitation but by way of illustration.

EXAMPLE 1

Measurement of anti-streptolysin O (ASO) value
(1) Modification of streptolysin O (SLO)

In 10 ml of 100 mM N-2-hydroxyethylpiperazine-N'-2-ethanesulfonic acid (HEPES) buffer (pH 8.5) was dissolved commercial SLO (available from Wako Pure Chemical Industries, Ltd.) to a concentration of 1.3 mg protein/ml. To the resulting solution was added 1 ml of a 40 mM solution of N-succinimidyl-4-nitrophenylacetate (SNPA, mfd. by DOJINDO LABORATORIES) in N,N-dimethylformamide, and the reaction was carried out at 37° C. for 2 hours. After completion of the reaction, the reaction solution was dialyzed against a 0.9% NaCl solution to remove the unreacted SNPA, whereby a modified SLO solution was obtained.
(2) Measurement of anti-streptolysin O (ASO) value
[Preparation of reagent solutions]
① First reagent solution As a first reagent solution, there was used 50 mM 3-(N-morpholino)propanesulfonic acid (MOPS)-NaOH buffer (pH 7.4) containing 3.5% polyethylene glycol 6,000, 0.9% NaCl and 0.1% $NAN_3$.
② Second reagent solution As a second reagent solution, there was used a solution prepared by adding the modified SLO obtained in (1) above to the first reagent solution to adjust the protein concentration to 150 µg/ml.
[Measuring instrument]

An Autoanalyzer Hitachi Model 7070 was used.
[Measuring procedure]

After 20 µl of a sample containing a predetermined concentration of ASO and 350 µl of the first reagent solution were mixed and then incubated at 37° C. for 5 minutes, absorbance using dual wavelength ($\lambda_1$=700 nm, $\lambda_2$=340 nm) was measured (sample blank value). Then, 50 µl of the second reagent solution was added and the resulting mixture was incubated at 37° C. for 5 minutes, after which absorbance using dual wavelength ($\lambda_1$=700 nm, $\lambda_2$=340 nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using unmodified SLO.
[Results]

FIG. 1 shows calibration curves each showing a relationship between the obtained absorbance due to reaction and ASO concentration. In FIG. 1, + shows the results obtained by use of the second reagent solution containing the modified SLO, and □ the results obtained by use of the second reagent solution containing unmodified SLO.

As is clear from FIG. 1, when unmodified SLO is used (a conventional method), the reaction sensitivity is lowered in a concentration range of 200 U/ml or less, so that the measurement becomes impossible. On the other hand, when the present invention's method using the modified SLO is employed, the reaction sensitivity is sufficient to carry out the measurement, even in a concentration range of 100 U/ml or less.

EXAMPLE 2

Measurement of rheumatoid factor (RF)
(1) Preparation of biotin-modified human IgG In 9 ml of 50 mM carbonate buffer (pH 9) was dissolved 100 mg of commercially available human IgG, followed by adding thereto a solution of 9 mg of biotinamidocaproate-N-hydroxysuccinimidoester (BAHS, mfd. by Pierce Chemical Co.) in 1 ml of N,N-dimethylformamide. The reaction was carried out at 5° C. for 24 hours. After completion of the reaction, the reaction solution was dialyzed against a 0.9% NaCl solution to remove unreacted BAHS, whereby biotin-modified human IgG was obtained.

(2) Measurement of rheumatoid factor (RF)
[Preparation of reagent solutions]
① First reagent solution
The same as the first reagent solution used in Example 1.
② Second reagent solution As a second reagent solution, there was used a solution prepared by adding the biotin-modified human IgG to physiological saline (0.9% NaCl) to adjust the protein concentration to 1 mg/ml.

[Measuring instrument]
An Autoanalyzer Hitachi Model 7070 was used.
[Measuring procedure]

After 14 µl of a sample containing a predetermined concentration of RF and 250 µl of the first reagent solution were mixed and then incubated at 37° C. for 5 minutes, absorbance using dual wavelength ($\lambda_1$=700 nm, $\lambda_2$=340 nm) was measured (sample blank value). Then, 125 µl of the second reagent solution was added and the resulting mixture was incubated at 37° C. for 5 minutes, after which absorbance using dual wavelength ($\lambda_1$=700 nm, $\lambda_2$=340 nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using human IgG not modified with biotin.

Figure 2:
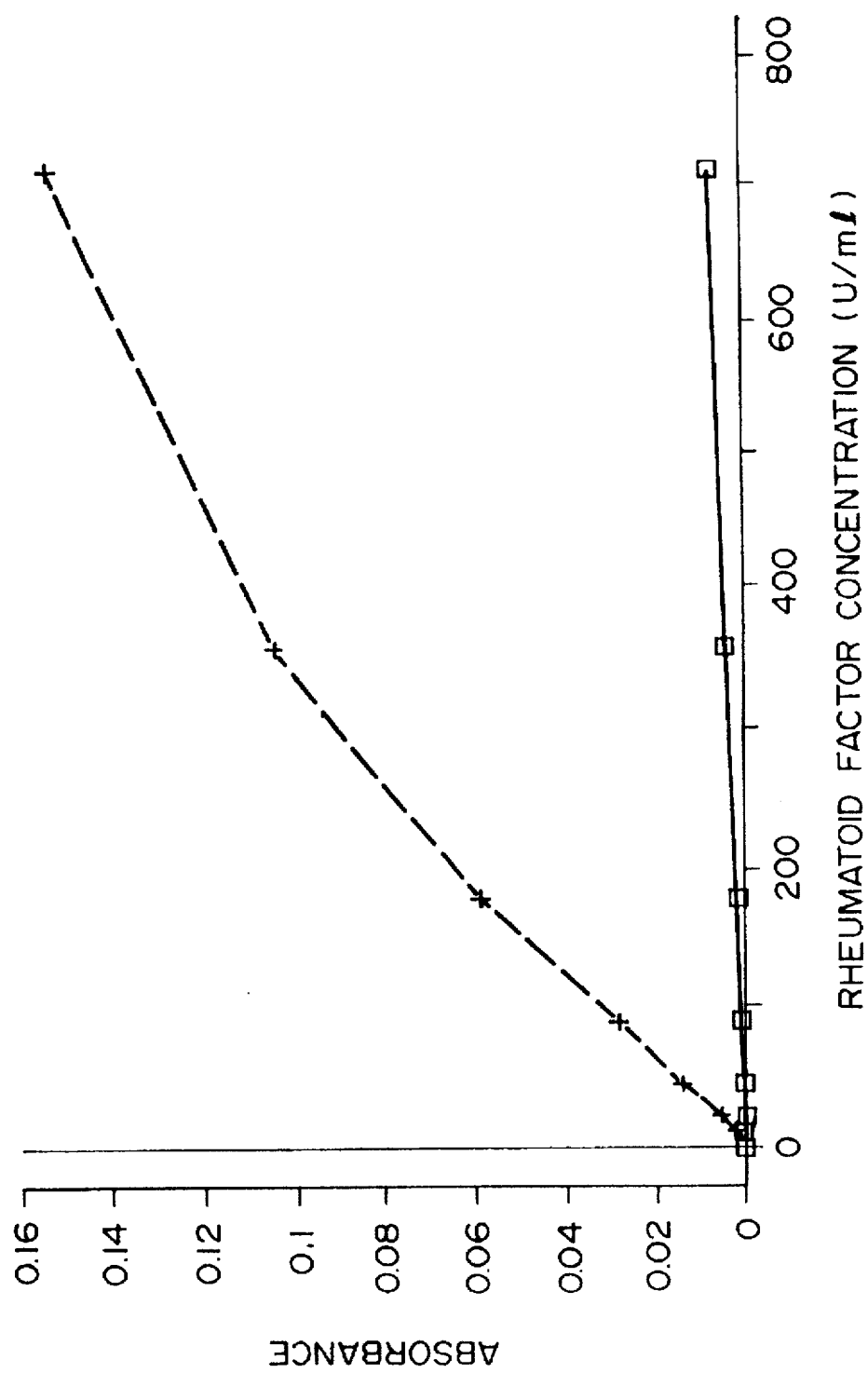
FIG. 2 shows a calibration curve obtained in Example 2.

[Results]
FIG. 2 shows calibration curves each showing a relationship between the obtained absorbance due to reaction and rheumatoid factor (RF) concentration. In FIG. 2, + shows the results obtained by use of the second reagent solution containing the biotin-modified human IgG, and □ the results obtained by use of the second reagent solution containing unmodified human IgG.

As is clear from FIG. 2, when unmodified human IgG is used (a conventional method), measurement of RF is difficult. On the other hand, when the present invention's method using the biotin-modified human IgG is employed, it becomes possible to measure RF with high sensitivity.

EXAMPLE 3

Measurement of anti-streptolysin O (ASO) value
(1) Preparation of biotin-modified streptolysin O (SLO)

In 30 mM phosphate buffer (pH 7.5) was dissolved commercially available SLO to a concentration of 1.3 mg protein/ml. To 5 ml of the resulting solution was added 0.5 ml of a 30 mM solution of N-hydroxysuccinimidobiotin (NHS-Biotin, mfd. by Pierce Chemical Co.) in N,N-dimethylformamide, and the reaction was carried out at 37° C. for 1 hours. After completion of the reaction, the reaction solution was dialyzed against a 0.9% NaCl solution to remove the unreacted NHS-Biotin, whereby biotin-modified SLO was obtained.

(2) Measurement of ASO
[Preparation of reagent solutions]
① First reagent solution
The same as in Example 1 was used.

② Second reagent solution

As a second reagent solution, there was used a solution prepared by adding the biotin-modified SLO obtained in (1) above to the first reagent solution to adjust the protein concentration to 150 µg/ml.

[Measuring instrument]
An Autoanalyzer Hitachi Model 7070 was used.
[Measuring procedure]

After 20 µl of a sample containing a predetermined concentration of ASO and 350 µl of the first reagent solution were mixed and then incubated at 37° C. for 5 minutes, absorbance using dual wavelength ($\lambda_1$=700 nm, $\lambda_2$=340 nm) was measured (sample blank value). Then, 50 µl of the second reagent solution was added and the resulting mixture was incubated at 37° C. for 5 minutes, after which absorbance using dual wavelength ($\lambda_1$=700 nm, $\lambda_2$=340 nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using unmodified SLO.

Figure 3:
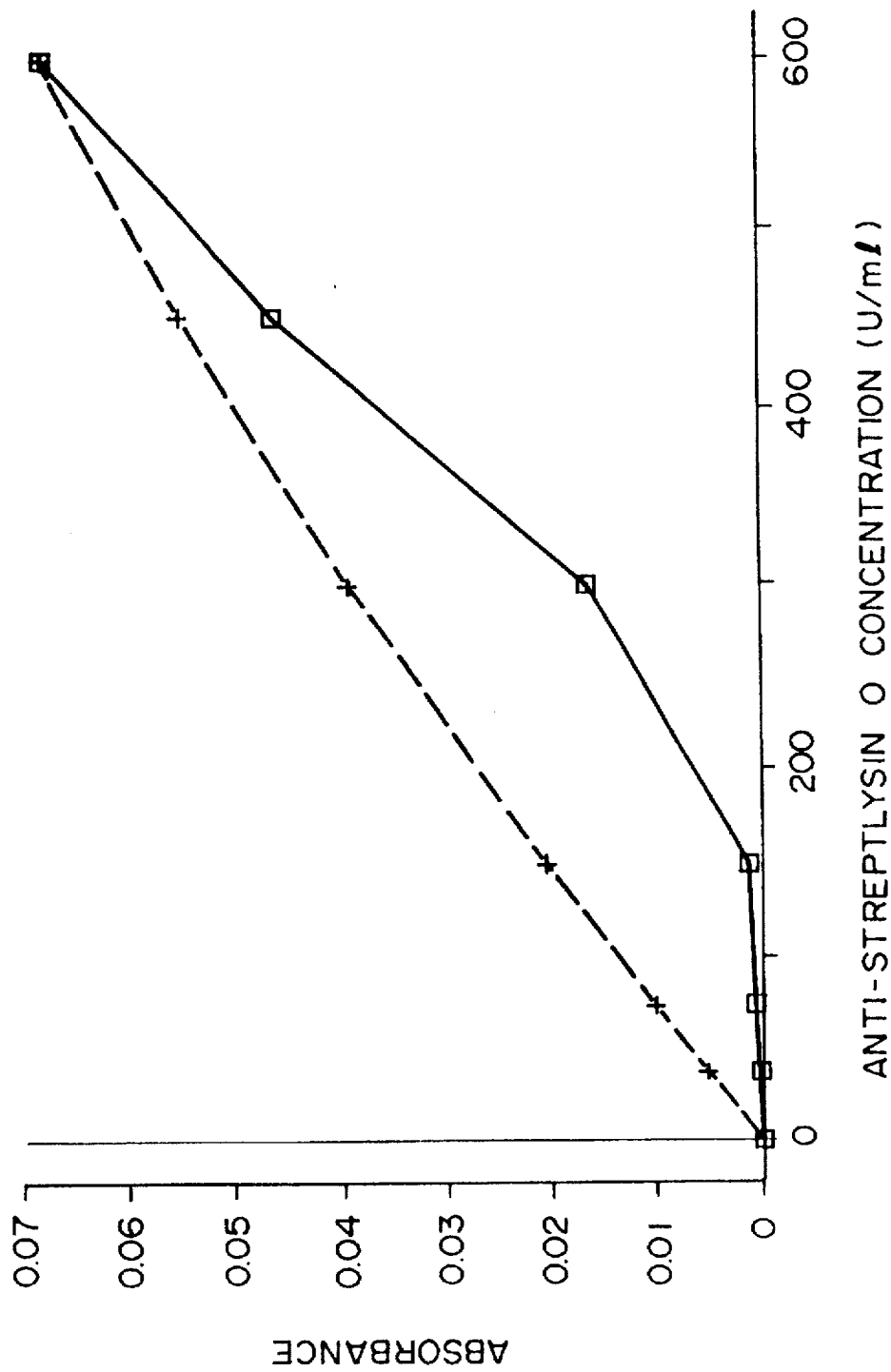
FIG. 3 shows a calibration curve obtained in Example 3.

[Results]
FIG. 3 shows calibration curves each showing a relationship between the obtained absorbance due to reaction and ASO concentration. In FIG. 3, + shows the results obtained by use of the second reagent solution containing the biotin-modified SLO, and □ the results obtained by use of the second reagent solution containing unmodified SLO.

As is clear from FIG. 3, when unmodified SLO is used (a conventional method), the reaction sensitivity is lowered in a concentration range of 150 U/ml or less, so that the measurement becomes impossible. On the other hand, when the present invention's method using the biotin-modified SLO is employed, the reaction sensitivity is sufficient even in a concentration range of 100 U/ml or less, so that a calibration curve showing good linearity can be obtained.

EXAMPLE 4

Measurement of anti-streptolysin O (ASO) value
(1) Modification of streptolysin O (SLO)

In 10 ml of 30 mM phosphate buffer (pH 7.5) was dissolved commercial SLO (available from Wako Pure Chemical Industries, Ltd.) to a concentration of 1.3 mg protein/ml. To the resulting solution was added 1 ml of a 30 mM solution of N-hydroxysuccinimidobiotin (NHS-biotin, mfd. by Pierce Chemical Co.) in N,N-dimethylformamide, and the reaction was carried out at 37° C. for 1 hours. After completion of the reaction, the reaction solution was dialyzed against a 0.9% NaCl solution to remove the unreacted NHS-biotin, whereby a biotin-modified SLO solution was obtained.

(2) Measurement of anti-streptolysin O (ASO) value
[Preparation of reagent solutions]
① Buffer solution for measurement As a buffer solution for measurement, there was used 50 mM 3-(N-morpholino)propanesulfonic acid (MOPS)-NaOH buffer (pH 7.4) containing 3.5% polyethylene glycol 6,000, 0.9% NaCl and 0.1% $NAN_3$.

② First reagent solution

As a first reagent solution, there was used a solution prepared by dissolving avidin (available from Wako Pure Chemical Industries, Ltd.) in the aforesaid buffer solution for measurement to adjust the protein concentration to 20 µg/ml.

③ Second reagent solution

As a second reagent solution, there was used a solution prepared by adding the biotin-modified SLO obtained in (1) above to the aforesaid buffer solution for measurement to adjust the protein concentration to 150 µg/ml.

[Measuring instrument]

An Autoanalyzer Hitachi Model 7070 was used.

[Measuring procedure]

After 20 µl of a sample containing a predetermined concentration of ASO and 350 µl of the first reagent solution were mixed and then incubated at 37° C. for 5 minutes, absorbance using dual wavelength ($\lambda_1$=700 nm, $\lambda_2$=340 nm) was measured (sample blank value). Then, 50 µl of the second reagent solution was added and the resulting mixture was incubated at 37° C. for 5 minutes, after which absorbance using dual wavelength ($\lambda_1$=700 nm, $\lambda_2$=340 nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using unmodified SLO.

[Results]

Figure 4:
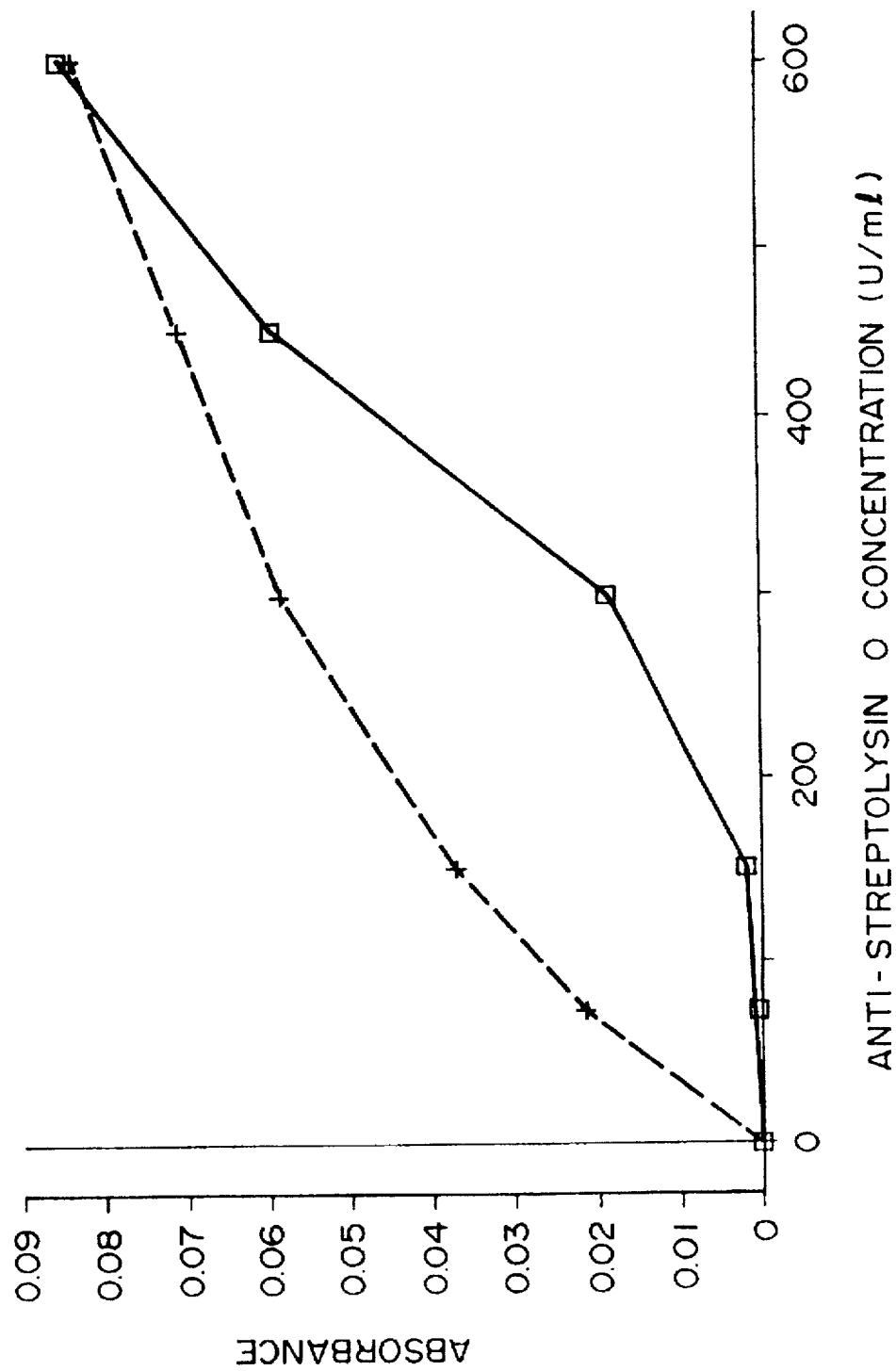
FIG. 4 shows a calibration curve obtained in Example 4.

FIG. 4 shows calibration curves each showing a relationship between the obtained absorbance due to reaction and ASO concentration. In FIG. 4, + shows the results obtained by use of the second reagent solution containing the modified SLO, and □ the results obtained by use of the second reagent solution containing unmodified SLO.

As is clear from FIG. 4, when unmodified SLO is used (a conventional method), the reaction sensitivity is lowered in a concentration range of 200 U/ml or less, so that the measurement becomes impossible. On the other hand, when the present invention's method using the modified SLO is employed, the reaction sensitivity is sufficient to carry out the measurement, even in a concentration range of 100 U/ml or less.

Referential Example 1

Preparation of anti-human C-reactive protein (anti-CRP) monoclonal antibody (1) immunization immunization was carried out by inoculating a mouse with commercial human CRP (available from Wako Pure Chemical Industries, Ltd.) three times at 2-week intervals (amount of human CRP per inoculating operation: 50 µg/mouse).

(2) Preparation of hybridoma

Three days after the final immunization, cell fusion between spleen cells removed from the mouse and myeloma cells (P3/NS1-1-Ag4-1) was carried out according to the method of Kohler and Milstein [Nature, vol. 256, 495(1975)]. Screening was carried out in the following manner.

Each well of a 96-wells microtiter plate was fed with 50 µl of a 0.2% solution of human CRP in 50 mM carbonate buffer (pH 9.6), followed by incubation at 37° C. for 1 hour, whereby the human CRP was fixed to the microtiter plate. Each well was washed with 10 mM phosphate buffered saline (pH 7.4) and then fed with 50 µl of each of the culture supernatants of hybridoma obtained by the cell fusion, and the reaction was carried out at 37° C. for 1 hour. Each well was washed with 10 mM phosphate buffered saline (pH 7.4) and then fed with 50 µl of peroxidase-labeled anti-mouse immunoglobulin antibody (available from DAKOPATTS, Denmark) properly diluted with 10 mM phosphate buffered saline (pH 7.4), and the reaction was carried out at 37° C. for 1 hour. After washing with 10 mM phosphate buffered saline (pH 7.4), each well was fed with 50 µl of citrate buffer (pH 4.9) containing 2 mg/ml of o-phenylenediamine and 0.017% of hydrogen peroxide and allowed to stand at room temperature for 10 minutes to carry out coloration reaction. Then, each well was fed with 6N sulfuric acid to stop the coloration reaction.

On the basis of the results obtained above, hybridoma capable of producing a culture supernatant reactive with human CRP was selected as parent hybridoma. The parent hybridoma was cloned by limiting dilution to establish clones 1-3 and 2-6 of hybridoma capable of producing anti-human CRP monoclonal antibody.

(3) Preparation of monoclonal antibodies

Three days after having been intraperitoneally injected with 0.5 ml of pristane (2,6,10,14-tetramethylpentadecane, mfd. by Wako Pure Chemical Industries, Ltd.), a mouse was intraperitoneally inoculated with 1×106 cells of the clone 1-3 or 2-6 obtained in (2) above. Twelve days after the inoculation with the hybridoma, the ascites accumulated in the abdominal cavity was collected. Then, 10 ml of the obtained ascites was subjected to 40% ammonium sulfate fractionation, followed by dyalysis against 10 mM phosphate buffered saline (pH 7.4) (1 liter×3 times). Thus, anti-human CRP monoclonal antibody solutions were obtained.

EXAMPLE 5

Measurement of C-reactive protein (CRP)

(1) Preparation of biotin-modified anti-human CRP monoclonal antibody

Biotin-modified anti-human CRP monoclonal antibody was obtained by the same procedure with the same reagents as in Example 4 except for using the anti-human CRP monoclonal antibody (the clone 1-3) obtained in Referential Example 1, in place of SLO.

(2) Measurement of C-reactive protein (CRP)

[Preparation of reagent solutions]

① Buffer solution for measurement

The same as in Example 4.

② First reagent solution

As a first reagent solution, there was used a solution prepared by dissolving avidin (available from Wako Pure Chemical Industries, Ltd.) in the aforesaid buffer solution for measurement to adjust the protein concentration to 50 µg/ml.

③ Second reagent solution

As a second reagent solution, there was used a solution prepared by adding the biotin-modified anti-human CRP monoclonal antibody obtained in (1) above and the anti-human CRP monoclonal antibody (the clone 2-6) obtained in Referential Example 1 to the aforesaid buffer solution for measurement to adjust the concentration of each protein to 1 µg/ml.

[Measuring instrument]

An Autoanalyzer Hitachi Model 7070 was used.

[Measuring procedure]

After 15 µl of a sample containing a predetermined concentration of CRP and 350 µl of the first reagent solution were mixed and then incubated at 37° C. for 5 minutes, absorbance using dual wavelength ($\lambda_1$=700 nm, $\lambda_2$=340 nm) was measured (sample blank value). Then, 50 µl of the second reagent solution was added and the resulting mixture was incubated at 37° C. for 5 minutes, after which absorbance using dual wavelength ($\lambda_1$=700 nm, $\lambda_2$=340 nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using the unmodified anti-human CRP monoclonal antibody (the clone 1-3) in place of the biotin-modified anti-human CRP monoclonal antibody.

[Results]

Figure 5:
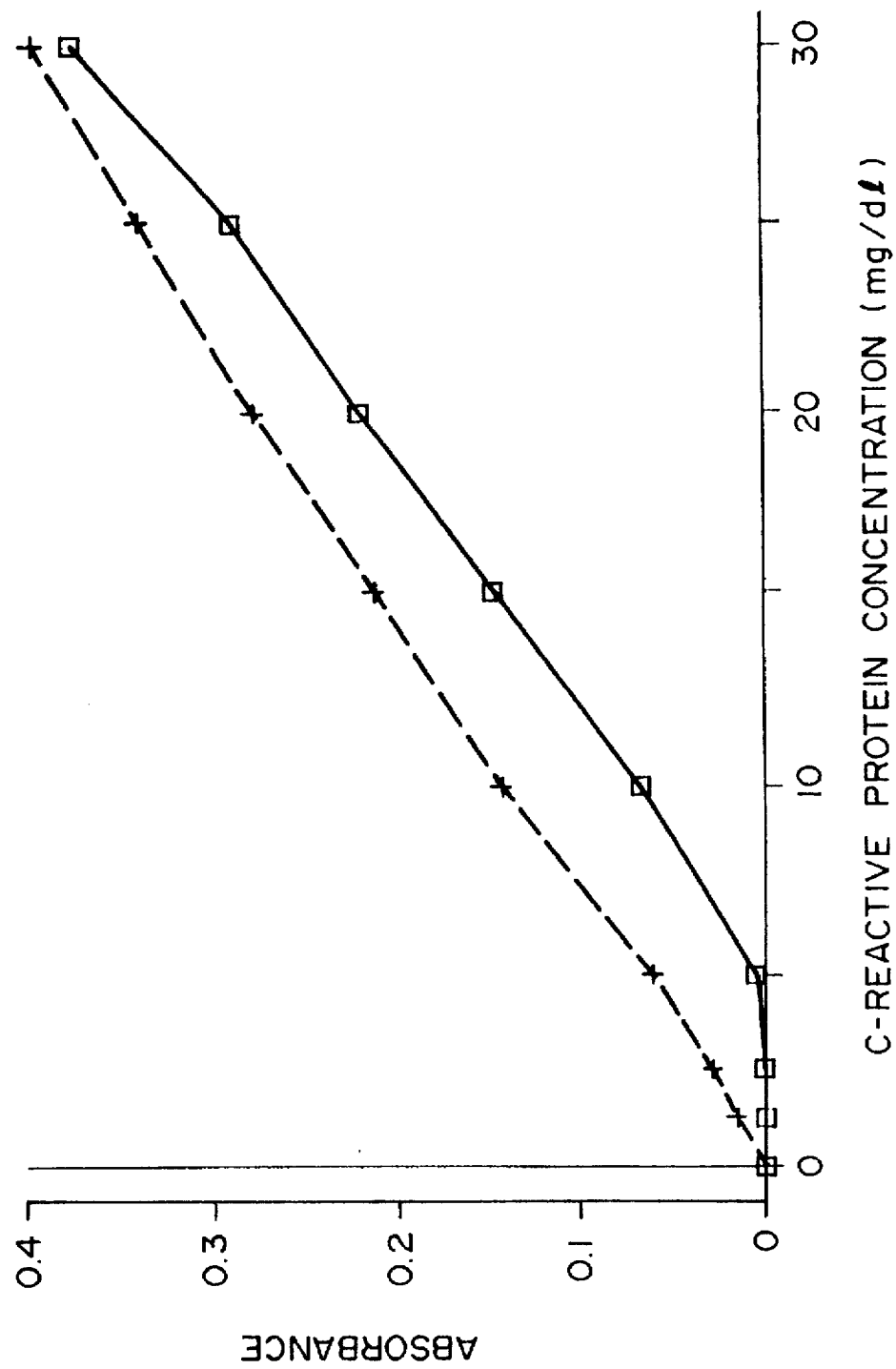
FIG. 5 shows a calibration curve obtained in Example 5.

FIG. 5 shows calibration curves each showing a relationship between the obtained absorbance due to reaction and CRP concentration. In FIG. 5, + shows the results obtained by use of the second reagent solution containing the biotin-modified anti-human CRP monoclonal antibody, and □ the results obtained by use of the second reagent solution containing the unmodified anti-human CRP monoclonal antibody alone.

As is clear from FIG. 5, when the second reagent solution containing the unmodified anti-human CRP monoclonal antibody alone is used (a conventional method), measurement of 5 mg/dl or less of CRP is difficult. On the other hand, when the present invention's method using the second reagent solution containing the biotin-modified anti-human CRP monoclonal antibody is employed, measurement of 5 mg/dl or less of CRP becomes possible.

EXAMPLE 6

Measurement of anti-human IgG antibody
(1) Preparation of biotin-modified human IgG In 9 ml of 50 mM carbonate buffer (pH 9) was dissolved 100 mg of commercially available human IgG, followed by adding thereto a solution of 9 mg of biotinamidocaproate-N-hydroxysuccinimidoester (BHS, mfd. by Pierce Chemical Co.) in 1 ml of N,N-dimethylformamide. The reaction was carried out at 5° C. for 24 hours. After completion of the reaction, the reaction solution was dialyzed against a 0.9% NaCl solution to remove unreacted BHS, whereby biotin-modified human IgG was obtained.

(2) Measurement of anti-human IgG antibody
[Preparation of reagent solutions]

① Buffer solution for measurement
The same as in Example 1.

② First reagent solution

As a first reagent solution, there was used a solution prepared by dissolving avidin (available from Wako Pure Chemical Industries, Ltd.) in the aforesaid buffer solution for measurement to adjust the protein concentration to 10 µg/ml.

③ Second reagent solution

As a second reagent solution, there was used a solution prepared by adding the biotin-modified human IgG obtained in (1) above to the aforesaid buffer solution for measurement to adjust the protein concentration to 75 µg/ml.

[Measuring instrument]

An Autoanalyzer Hitachi Model 7070 was used.

[Measuring procedure]

After 20 µl of a sample containing a predetermined concentration of anti-human IgG antibody and 350 µl of the first reagent solution were mixed and then incubated at 37° C. for 5 minutes, absorbance using dual wavelength ($\lambda_1=700$ nm, $\lambda_2=340$ nm) was measured (sample blank value). Then, 50 µl of the second reagent solution was added and the resulting mixture was incubated at 37° C. for 5 minutes, after which absorbance using dual wavelength ($\lambda_1=700$ nm, $\lambda_2=340$ nm) was measured. Absorbance difference (absorbance due to reaction) was calculated by subtracting the sample blank value corrected for solution volume from the thus obtained absorbance.

For comparison, absorbance due to reaction was measured by the same procedure as above by use of the same sample and reagent solutions as above except for using a second reagent solution prepared in the same manner as above except for using unmodified human IgG.

[Results]

Figure 6:
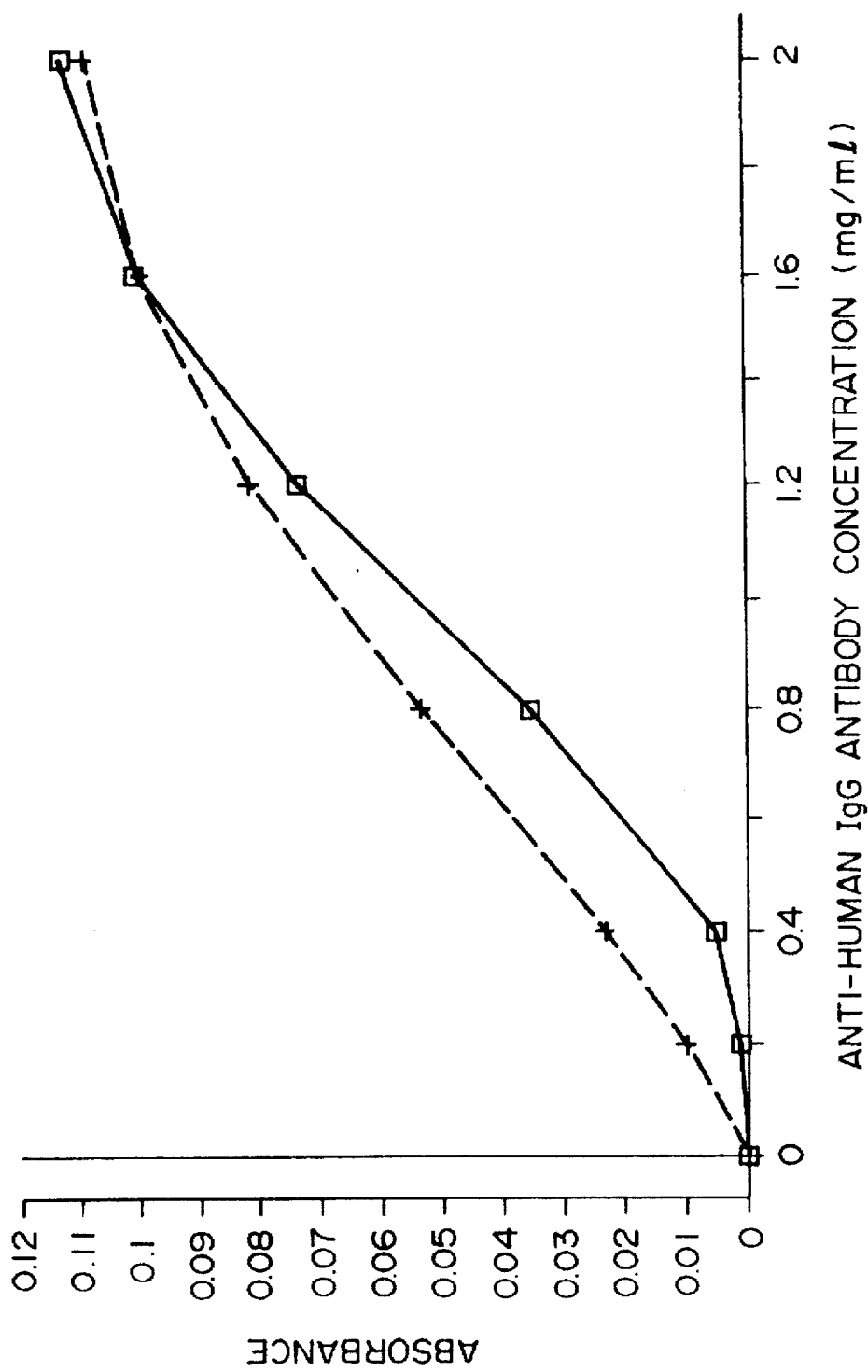
FIG. 6 shows a calibration curve obtained in Example 6.

FIG. 6 shows calibration curves each showing a relationship between the obtained absorbance due to reaction and anti-human IgG antibody concentration. In FIG. 6, + shows the results obtained by use of the second reagent solution containing the biotin-modified human IgG, and □ the results obtained by use of the second reagent solution containing unmodified human IgG.

As is clear from FIG. 6, the calibration curve obtained by the present invention's method using the second reagent solution containing the biotin-modified human IgG does not show curvature in a low concentration range, as compared with the calibration curve obtained in the case of using the second reagent solution containing unmodified human IgG (a conventional method). From the results shown in FIG. 6, it can also be seen that the method of this invention permits measurement of 0.2 mg/ml or less of anti-human IgG antibody.

As described above, this invention provides a method which permits accurate, highly-reproducible, rapid and easy measurement of an analyte to be measured, even in a low concentration range in which the analyte cannot be measured by a conventional method. Therefore, this invention contributes greatly to the art.

What is claimed is:

1. A method for immunoassay of a trace component in a body fluid, which comprises
reacting a body fluid sample containing the trace component which is an antibody with an antigen which binds to the trace component, said antigen being previously modified with a compound having a benzene ring or a compound having a heterocyclic ring,
measuring a change of turbidity or scattered light intensity caused by the reaction between the modified antigen and the trace component, and
determining the amount of trace component on the basis of the change of turbidity or scattered light.

2. A method according to claim 1, wherein the compound having a benzene ring is a compound having a substituted or unsubstituted phenyl, tolyl, xylyl or naphthyl group.

3. A method according to claim 1, wherein the compound having a heterocyclic ring is a compound having a substituted or unsubstituted thiazolyl, thienyl, furanyl, pyranyl, pyrrolyl, imidazolyl, pyrazolyl, isothiazolyl, isoxazolyl, pyrimidinyl, pyridazinyl, indolyl, purinyl, quinolyl, isoquinolyl, pyrazolinyl, indolinyl, morpholino, or biotinyl group.

4. A method according to claim 1, wherein the hapten is biotin.

5. A method according to claim 4, wherein the immunoassay is carried out in the presence of avidin or streptoavidin.

6. A method for immunoassay of a trace component in a body fluid, which comprises
reacting a body fluid sample containing the trace component which is an antigen with an antibody which binds to the trace component, said antibody being previously modified with a compound having a benzene ring or a compound having a heterocyclic ring.

measuring a change of turbidity or scattered light intensity caused by the reaction between the modified antibody and the trace component, and determining the amount of trace component on the basis of the change of turbidity or scattered light.

7. A method according to claim 6, wherein the compound having a benzene ring is a compound having a substituted or unsubstituted phenyl, tolyl, xylyl or naphthyl group.

8. A method according to claim 6, wherein the compound having a heterocyclic ring is a compound having a substituted or unsubstituted thiazolyl, thienyl, furanyl, pyranyl, pyrrolyl, imidazolyl, pyrazolyl, isothiazolyl, isoxazolyl, pyrimidinyl, pyridazinyl, indolyl, purinyl, quinolyl, isoquinolyl, pyrazolinyl, indolinyl, morpholino, or biotinyl group.

9. A method according to claim 6, wherein the hapten is biotin.

10. A method according to claim 9, wherein the immunoassay is carried out in the presence of avidin or streptoavidin.

* * * * *